United States Patent
Desfougeres et al.

(10) Patent No.: US 9,725,691 B2
(45) Date of Patent: Aug. 8, 2017

(54) YEAST STRAINS CAPABLE OF METABOLIZING XYLOSE AND RESISTANT TO INHIBITORS, METHOD FOR OBTAINING SAME AND USE THEREOF

(71) Applicant: LESAFFRE ET COMPAGNIE, Paris (FR)

(72) Inventors: Thomas Desfougeres, Neuville En Ferrain (FR); Georges Pignede, Marcq-en-baroeul (FR)

(73) Assignee: LESAFFRE ET COMPAGNIE, Paris (FR)

( * ) Notice: Subject to any disclaimer, the term of this patent is extended or adjusted under 35 U.S.C. 154(b) by 97 days.

(21) Appl. No.: 14/403,572

(22) PCT Filed: May 24, 2013

(86) PCT No.: PCT/FR2013/051137
§ 371 (c)(1),
(2) Date: Nov. 24, 2014

(87) PCT Pub. No.: WO2013/178915
PCT Pub. Date: Dec. 5, 2013

(65) Prior Publication Data
US 2015/0104822 A1    Apr. 16, 2015

(30) Foreign Application Priority Data
Jun. 1, 2012 (FR) .................... 12 55076

(51) Int. Cl.
| | |
|---|---|
| *C12P 7/06* | (2006.01) |
| *C12N 1/16* | (2006.01) |
| *C12R 1/865* | (2006.01) |
| *C12N 1/36* | (2006.01) |
| *C12P 7/10* | (2006.01) |

(52) U.S. Cl.
CPC .................. *C12N 1/16* (2013.01); *C12N 1/36* (2013.01); *C12P 7/06* (2013.01); *C12P 7/10* (2013.01); *C12R 1/865* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | |
|---|---|---|
| 2012/0142067 A1 | 6/2012 | Desfougeres et al. |
| 2013/0040353 A1 | 2/2013 | Desfougeres et al. |

FOREIGN PATENT DOCUMENTS

| | | |
|---|---|---|
| WO | 2011/128552 | 10/2011 |
| WO | 2012/072793 | 6/2012 |

OTHER PUBLICATIONS

Matsushika et al., Appl Microbiol Biotechnol (2009) 84:37-53.*
XXIIIrd International Conference on Yeast Genetics and Molecular Biology S43 01—Yeasts in brewing, wine and biotechnology, 2007.*
Attfield et al., FEMS Yeast Res 6 (2006) 862-868.*
International Search Report dated Aug. 14, 2013, which issued during prosecution of International Application No. PCT/FR2013/051137.
Sanda, et al. "Repeated-batch fermentation of lignocellulosic hydrolysate to ethanol using a hybrid *Saccharomyces cerevisiae* strain metabolically engineered for tolerance to acetic and formic acids" Bioresource Technology 102(17): 7917-7924, Jun. 2011.

* cited by examiner

*Primary Examiner* — Irene Marx
(74) *Attorney, Agent, or Firm* — Vedder Price P.C.; Thomas J. Kowalski; Deborah L. Lu

(57) ABSTRACT

The subject matter of the present invention is novel yeast strains capable of metabolizing xylose and resistant to at least one fermentation inhibitor, and also to the method of obtaining same. The subject of the present invention is also the yeasts obtained by culturing said yeast strains and the use thereof for producing at least one fermentation product, preferably ethanol, in particular in a culture medium comprising xylose and at least one fermentation inhibitor.

3 Claims, 2 Drawing Sheets

YEAST STRAINS CAPABLE OF METABOLIZING XYLOSE AND RESISTANT TO INHIBITORS, METHOD FOR OBTAINING SAME AND USE THEREOF

RELATED APPLICATIONS

The present application is filed pursuant to 35 U.S.C. §371 as a U.S. National Phase application of International Patent Application No. PCT/FR2013/051137, which was filed on May 24, 2013, claiming the benefit of priority to French Patent Application No. FR 12 55076 filed on Jun. 1, 2012. The entire content of each of the aforementioned patent applications is incorporated herein by reference in its entirety.

TECHNICAL FIELD

The present invention relates to the field of yeast strains capable of metabolizing xylose and also exhibiting resistance to at least one fermentation inhibitor, to the method for obtaining same, to the yeasts obtained from said yeast strains and to the use thereof for producing a fermentation product in a medium comprising xylose, optionally in the presence of at least one fermentation inhibitor.

TECHNOLOGICAL BACKGROUND

Document PCT/EP2011/071616 describes yeasts for producing alcohol in media containing at least one pentose, via the expression of the XI-XDH metabolic pathway. Said document describes for the first time the combination of an overexpression of xylose isomerase (XI) activity with an overexpression of xylitol dehydrogenase (XDH) activity and shows that the overexpression of xylitol dehydrogenase activity makes it possible to prevent the inhibition, by xylitol, of xylose isomerase activity. Document PCT/EP2011/071616 describes, for example, the yeast strain deposited at the CNCM [National Collection of Microorganism Cultures] on Oct. 5, 2011, under number I-4538.

The industrial production of alcohol by yeast from lignocellulosic hydrolyzates requires not only the genetic machinery for metabolizing pentoses, but also properties of resistance to the fermentation inhibitors present in these lignocellulosic hydrolyzates.

The fermentation inhibitors are produced during the pretreatment and the hydrolysis of the lignocellulosic biomass. Among the fermentation inhibitors are furaldehydes (furfural. HMF), phenolic compounds and organic acids (acetic acid, levulinic acid, formic acid).

Various means have been described for countering the effect of fermentation inhibitors, among which are detoxification of the fermentation medium, improvement of the fermentation process, or improvement of the resistance of yeasts to fermentation inhibitors.

The resistance of yeasts to fermentation inhibitors has, for example, been improved genetically, by directed evolution or by acclimatization (Almeida and Hahn-Hägerdal, International Sugar Journal, 2009. Vol. 111, No. 1323).

However, it appears to be difficult to provide an industrial yeast strain which gives yeasts which are both effective for alcohol production in a fermentation medium comprising at least one pentose, and resistant to at least one fermentation inhibitor.

There is thus a real need to provide novel yeast strains which are capable of metabolizing at least one pentose, for example xylose, even in the presence of at least one fermentation inhibitor, such as acetic acid, said yeast strains giving yeasts which are effective for producing alcohol, even in the presence of at least one fermentation inhibitor.

SUMMARY OF THE INVENTION

A first object of the invention relates to the yeast strain deposited at the CNCM [National Collection of Microorganism Cultures] under number I-4627.

A second object of the invention relates to a method for obtaining a yeast strain capable of metabolizing xylose and resistant to acetic acid, comprising the steps of:
crossing the yeast strain deposited at the CNCM [National Collection of Microorganism Cultures] under number I-4538 with the yeast strain deposited at the CNCM under number I-4627, so as to obtain at least one hybrid.
selecting at least one hybrid capable of metabolizing xylose and resistant to acetic acid.

A third object of the invention relates to a yeast strain capable of metabolizing xylose and resistant to acetic acid, which can be obtained by means of the method as defined above.

A fourth object of the invention relates to a yeast strain derived from a yeast strain as defined above, characterized in that said derived yeast strain is capable of metabolizing xylose and resistant to acetic acid.

A fifth object of the invention relates to a yeast obtained by culturing a yeast strain as defined above or by culturing a derived yeast strain as defined above.

A sixth object of the invention relates to a method for producing at least one fermentation product, comprising a step of fermentation, under anaerobic conditions, using a yeast as defined above.

A seventh object of the invention relates to the use of a yeast as defined above, for producing at least one fermentation product, preferably in a fermentation medium comprising xylose and/or one fermentation inhibitor.

DEPOSITS

The Deposits with Collection Nationale de Cultures de Microorganisme (CNCM), under deposit accession numbers I-4538, I-4624 and I-4627 and were made pursuant to the terms of the Budapest Treaty. Upon issuance of a patent, all restrictions upon the deposit will be removed, and the deposit is intended to meet the requirements of 37 CFR §§1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

DEFINITIONS

Figure 1:
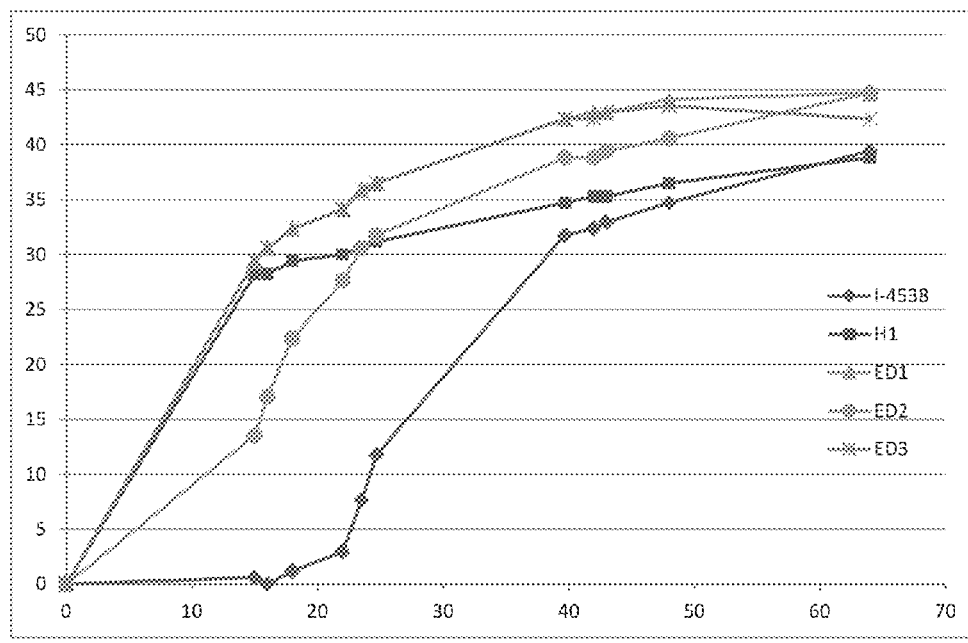
FIG. 1: Ethanol production (in g/kg of fermentation medium) over time (in hours) in the YFGX-Ac fermentation medium, at 32° C., by the I-4538 yeast strain (diamond), the H1 yeast strain (square), the ED1 yeast strain (triangle), the ED2 yeast strain (circle) and the ED3 yeast strain (cross).

The expression "yeast strain" denotes a relatively homogeneous population of yeast cells.

A yeast strain is obtained from the isolation of a clone, a clone being a cell population obtained from a single yeast cell.

The term "exogenous" gene is intended to mean a gene which is not naturally present in a yeast strain of the species under consideration.

The term "endogenous" gene is intended to mean a gene which is naturally present in a yeast strain of the species under consideration.

A xylose isomerase or XI denotes herein an enzyme capable of converting, in a single step, D-xylose to D-xylulose and which corresponds to the class EC 5.3.1.5.

A xylitol dehydrogenase or XDH denotes herein an enzyme capable of converting, in a single step, xylitol to D-xylulose and which corresponds to the class EC 1.1.1.9.

Xylose reductase or XR denotes herein an enzyme capable of converting, in a single step, D-xylose to xylitol and which corresponds to the class EC 1.1.1.307.

A D-xylulokinase or XKS denotes herein an enzyme capable of converting, in a single step.

D-xylulose to D-xylulose-5-phosphate and which corresponds to the class EC 2.7.1.17.

The GRE3 gene encodes an aldose reductase enzyme which corresponds to the class EC 1.1.1.21.

The RPE1 gene encodes a D-ribulose-5-phosphate 3-epimerase enzyme which corresponds to the class EC 5.1.3.1.

The RKI1 gene encodes a ribose-5-phosphate ketol-isomerase enzyme which corresponds to the class EC 5.3.1.6.

The TKL1 gene encodes a transketolase enzyme which corresponds to the class EC 2.2.1.1.

The TAL1 gene encodes a transaldolase enzyme which corresponds to the class EC 2.2.1.2.

A prototrophic yeast strain is a yeast strain capable of growing on a minimum medium. In particular, a prototrophic yeast strain according to the invention is capable of synthesizing all the amino acids and bases required for its growth.

A minimum medium is a medium comprising a carbon source ($C_xH_yO_z$), an inorganic nitrogen source, a potassium source, a phosphorus source, a sulfur source, a magnesium source, a calcium source, an iron source, a trace element source and water.

An example of minimum medium is the YNB (Yeast Nitrogen Base) medium to which a carbon source (for example a sugar) and an inorganic nitrogen source (for example ammonium sulfate) are added.

The YNB medium comprises, per liter: 2 µg biotin, 400 µg calcium pantothenate, 2 µg folic acid, 2000 µg inositole, 400 µg niacin, 200 µg p-aminobenzoic acid, 400 µg pyridoxine hydrochloride, 200 µg riboflavin, 400 µg thiamine hydrochloride, 500 µg boric acid, 40 µg copper sulfate, 100 µg potassium iodide, 200 µg ferric chloride, 400 µg manganese sulfate, 200 µg sodium molybdenate, 400 µg zinc sulfate, 1 g monobasic potassium phosphate, 500 mg magnesium sulfate, 100 mg sodium chloride, 100 mg calcium chloride, 5 g/l ammonium sulfate, final pH 5.4.

The expression "derived yeast strain" denotes a yeast strain derived by one or more crosses and/or by mutation and/or by genetic transformation.

A yeast strain derived by crossing can be obtained by crossing a yeast strain according to the invention with the same yeast strain, with another yeast strain according to the invention, or with any other yeast strain.

A yeast strain derived by mutation can be a yeast strain having undergone at least one spontaneous mutation in its genome or at least one mutation induced by mutagenesis. The mutation(s) of a derived strain may or may not be silent.

The expression "mutagenesis" denotes both random mutagenesis obtained by applying radiation (for example UV radiation) or using mutagenic chemical agents, and insertion or side-directed mutagenesis, by transposition or by integration of an exogenous DNA fragment.

A yeast strain derived by genetic transformation is a yeast strain into which has been introduced a DNA sequence which is preferably provided by a plasmid or integrated directly into the genome.

DETAILED DESCRIPTION OF THE INVENTION

The goal of the present invention is to provide a yeast strain capable of metabolizing at least one pentose, in particular xylose, even in the presence of at least one fermentation inhibitor, such as acetic acid.

For the purposes of the invention, a yeast strain capable of metabolizing xylose is a yeast strain capable of producing ethanol in a medium comprising xylose, under anaerobic conditions.

In particular, a yeast strain capable of metabolizing xylose is a yeast strain capable of converting xylose to ethanol. i.e. capable of fermenting xylose.

The conversion of xylose to ethanol results from the direct or indirect isomerization of xylose to xylulose, followed by the use of the resulting xylulose in the nonoxidative part of the pentose phosphate pathway.

For the purposes of the invention, a yeast strain capable of metabolizing xylose is a yeast strain which converts at least 70%, preferably at least 80%, more preferentially at least 90% of the xylose to ethanol in 60 hours in a fermentation medium comprising 55 g of glucose and 45 g of xylose per kg of fermentation medium, under anaerobic conditions.

The inoculation with the yeast strain used to measure the percentage of xylose converted to ethanol is preferably 0.25 g of dry matter/kg of fermentation medium.

The period of 60 hours is calculated starting from the inoculation of the yeast strain into the fermentation medium.

The fermentation medium used to measure the percentage of xylose converted to ethanol is preferably a synthetic medium.

A synthetic medium is a medium of which the exact chemical composition is known.

A synthetic medium according to the invention comprises a carbon source, a nitrogen source, a phosphorus source, and also the vitamins and minerals essential for the growth of a yeast strain.

In one preferred embodiment, the fermentation medium used to measure the percentage of xylose converted to ethanol is the YFGX synthetic medium comprising 55 g/kg of glucose, 45 g/kg of xylose, 10 g/kg of yeast extract, 10 g/kg of petone and 2000 ppm of acetic acid, the pH being adjusted to 5 with KOH.

In the YFGX medium, the acetic acid present at a concentration of 2000 ppm at pH 5 has no inhibitory effect.

The fermentation is preferably carried out at 32° C., with moderate stirring, for example 90 rpm.

The stirring is moderate so as not to be oxygenating.

The pH of the medium is preferably controlled, for example by the buffering capacity of an acid/base pair, for example the acetic acid/acetate buffering capacity in the YFGX medium.

The amount of ethanol present in the fermentation medium is measured by any appropriate means known to those skilled in the art.

It may involve a direct measurement of the ethanol produced or an indirect measurement via a parameter which correlates with ethanol production, such as the loss of mass.

For example, the alcohol production can be measured by chromatography, in particular by HPLC (High Performance Liquid Chromatography), an enzymatic kit (for example the ethanol assaying kit from Boehringer), or an assay using potassium dichromate.

The amount of xylose present in the fermentation medium is measured by any appropriate means known to those skilled in the art, preferably by chromatography, in particular by HPLC.

The use of a fermentation medium comprising both glucose and xylose makes it possible to evaluate the conversion of xylose to ethanol using a quantity of biomass which is comparable for the various yeast strains evaluated. Indeed, the yeast strains first ferment the glucose of the glucose and xylose mixture, and then the glucose and the xylose.

The capacity to metabolize xylose in the presence of at least one fermentation inhibitor is described as a resistance to said fermentation inhibitor.

In the context of the present invention, the fermentation inhibitor is preferably acetic acid.

It is the nonionized form of acetic acid, starting from a certain concentration, termed toxic concentration, which is responsible for its toxicity and therefore for its inhibitory effect.

For example, a concentration of 4000 ppm of acetic acid at pH 4.4 is a toxic concentration for strains not resistant to acetic acid, such as the I-4538 yeast strain.

During fermentation under anaerobic conditions, the inhibitory effect of acetic acid results in particular in a delay of the initiation of the conversion of the sugars to biomass and to ethanol.

The resistance to acetic acid is measured herein relative to the delay of initiation of the conversion of the sugars to ethanol, i.e. to the delay of initiation of alcoholic fermentation.

The alcoholic fermentation curve representing the amount of alcohol produced as a function of time generally comprises three phases:
  a latency phase, during which there is no ethanol production,
  an alcohol production phase, and
  a plateau phase, which corresponds to the end of the fermentation.

The delay of the initiation of alcoholic fermentation corresponds herein to the x-axis at the origin of the line representing the maximum derivative of the alcohol production rate.

More simply, the delay of the initiation of alcoholic fermentation corresponds herein to the x-axis at the origin of the line corresponding to the slope of the alcohol production phase.

A yeast strain resistant to acetic acid is defined herein as a yeast strain having a delay of initiation of alcoholic fermentation of less than 30 hours, preferably less than 29 hours, more preferentially less than 28 hours, in a fermentation medium comprising 4000 ppm of acetic acid at pH 4.4.

The fermentation medium used for evaluating the resistance to acetic acid is preferably a synthetic medium, more preferentially the YFAc medium.

The composition of the YFAc medium is the following: 150 g/kg of glucose, 5 g/kg of yeast extract, 4.7 g/kg of DAP (diammonium phosphate), 11.5 g/kg of citric acid, 4 g/kg of acetic acid, 13.5 g/kg of sodium citrate, 1 ml/kg of Tween 80, 2 ml/kg of $ZnSO_4$ (at 10.6 g/l), 2.5 ml/kg of $MgSO_4.7H_2O$ (at 400 g/l), 1 ml/kg of thiamine (at 18.24 g/l), 1 ml/kg of pyridoxine (at 5.28 g/l), 1 ml/kg of biotin (at 1.76 g/l), 1 ml/kg of pantothenate (at 3.8 g/l), 2.5 ml/kg of nicotinic acid (at 8 g/l), 1 ml/kg of mesoinositol (at 50 g/1), 1 ml kg of riboflavin (at 1 g/l), 1 ml/kg of para-aminobenzoate (at 1.2 g/l), pH adjusted to 4.4 with KOH.

The inoculation with the yeast strain used for evaluating the resistance to acetic acid is preferably 0.25 g of dry matter/kg of fermentation medium.

The time t=0 of the alcoholic fermentation curve corresponds to the time at which the yeast strain is inoculated into the fermentation medium.

The alcoholic fermentation is carried out under anaerobic conditions, preferably at 32° C. and with moderate stirring, for example 90 rpm.

The stirring is moderate so as not to be oxygenating.

The pH of the medium is preferably controlled, for example by the buffering capacity of an acid/base pair, for example the acetic acid/acetate buffering capacity in the YFAc medium.

In the YFAc fermentation medium, a yeast strain not resistant to acetic acid can have a delay of initiation of alcoholic fermentation of at least 40 h.

The inventors have sought to obtain a yeast strain capable of metabolizing xylose, even in the presence of acetic acid, starting from a yeast strain which is effective in terms of conversion to of xylose to ethanol.

This yeast strain which is effective in terms of conversion of xylose to ethanol, chosen as starting strain to be improved with a view to conferring thereon a characteristic of resistance to acetic acid, is the I-4538 yeast strain deposited under the treaty of Budapest on Oct. 5, 2011, with the CNCM (National Collection of Microorganism Cultures), 25, rue du Docteur Roux, 75724 Paris cedex 15, France.

The I-4538 yeast strain converts at least 90% of xylose to ethanol in 60 hours in the YFGX fermentation medium comprising 55 g of glucose and 45 g of xylose per kg of medium.

However, the I-4538 yeast strain is particularly sensitive to acetic acid; it has a delay of initiation of alcoholic fermentation of at least 40 hours in a YFAc fermentation medium comprising 4000 ppm of acetic acid at pH 4.4.

The I-4538 yeast strain is a *Saccharomyces cerevisiae* strain obtained by directed evolution from a yeast strain genetically modified by:
  the insertion of at least one copy of an exogenous gene encoding a xylose isomerase (XI) of *Clostridium phytofermentans*, under the control of the pADH1 promoter and of the CYC1 terminator, the insertion of at least one copy of an exogenous gene encoding a xylitol dehydrogenase (XDH) of *Pichia stipitis*, under the control of the pADH1 promoter and of the CYC1 terminator, at least one copy of the TAL1 endogenous gene placed under the control of the pPGK1 promoter, at least one copy of the TKL1 endogenous gene placed under the control of the pTDH3 promoter, at least one copy of the RPE1 endogenous gene placed under the control of the pTDH3 promoter.

at least one copy of the RKI1 endogenous gene placed under the control of the pTDH3 promoter, the insertion of at least one copy of an endogenous gene encoding a xylulokinase (XKS1) under the control of the pADH1 promoter and of the CYC1 terminator, and the deletion of at least one copy of the open reading frame of the GRE3 endogenous gene encoding an aldose reductase.

The I-4538 yeast strain is devoid of any residual selectable marker.

The I-4538 yeast strain does not comprise a gene encoding an XR of exogenous origin, nor an araA, araB or AraD gene.

The exogenous gene encoding a xylose isomerase (XI) of *Clostridium phytofermentans* is described in document DE102008031350.

The exogenous gene encoding a xylitol dehydrogenase (XDH) of *Pichia stipitis* is in Genbank.

The exogenous gene encoding a xylitol dehydrogenase (XDH) of *Pichia stipitis* is the gene of reference sequence X55392.1 on Genbank.

The pADH1, pPGK1 and pTDH3 promoters are promoters of *Saccharomyces cerevisiae*.

The CYC1 terminator is a promoter of *Saccharomyces cerevisiae*.

The I-4538 yeast strain is an industrial yeast strain which is aneuploid.

The I-4538 yeast strain is prototrophic.

In order to confer a property of resistance to acetic acid on the I-4538 yeast strain, but without substantially modifying its ability to metabolize xylose, the inventors have chosen to use the strain crossing technique.

To the knowledge of the inventors, it is the first time that the crossing technique is used to improve a genetically modified aneuploid yeast strain.

Indeed, those skilled in the art would not at first glance envision using the crossing technique, when the starting yeast strain:

comprises no fewer than eight genetic modifications which must a priori be transferred to the selected segregants, is an aneuploid yeast strain and there are segregation problems in the absence of strict diploidy, and has undergone a step of mutagenesis in the context of directed evolution, which may be responsible for difficulties for the crosses, in particular in the case of chromosomal translocation responsible for germination problems.

Crosses were thus carried out between the I-4538 yeast strain and yeast strains which are resistant to acetic acid and not genetically modified, i.e. do not possess the genetic machinery required for xylose fermentation.

The yeast strains resistant to acetic acid, used for the crosses, have a delay of initiation of alcoholic fermentation of less than 14 h in the YFAc fermentation medium.

The results of the crosses were not conclusive: while the characteristic of resistance to acetic acid was indeed transferred to the hybrids, the latter were much less effective than the starting I-4538 yeast strain for converting xylose to ethanol.

At best, the hybrids obtained converted 40% of the xylose to ethanol in 60 hours in the YFGX fermentation medium comprising 55 g of glucose and 45 g of xylose per kg of medium.

The inventors tried to improve the xylose fermentation of these hybrids by directed evolution, but without further success.

The inventors have therefore demonstrated that, in order to transfer the characteristic of resistance to acetic acid by crossing, without losing the ability to efficiently metabolize xylose, it is necessary to cross the I-4538 yeast strain with a yeast strain resistant to acetic acid which has a similar genetic background, i.e. which also has the genetic machinery for metabolizing xylose, but without necessarily being effective in terms of metabolizing xylose.

The yeast strain used, which both is resistant to acetic acid and also has the genetic machinery for metabolizing xylose, is the *Saccharomyces cerevisiae* strain deposited under number I-4627 under the treaty of Budapest on May 24, 2012, with the CNCM (National Collection of Microorganism Cultures), 25, rue du Docteur Roux, 75724 Paris cedex 15, France. Thus, by crossing the I-4538 yeast strain with the I-4627 yeast strain, the inventors have obtained yeast strains which are both effective for metabolizing xylose and resistant to acetic acid.

An object of the present invention is thus the yeast strain deposited with the CNCM under number I-4627.

The I-4627 strain constitutes one of the two starting strains for obtaining the yeast strains according to the invention.

The I-4627 yeast strain is a novel yeast strain, obtained by means of an original method of crossing an aneuploid yeast strain which is resistant to acetic acid and not genetically modified, with a genetically modified aneuploid yeast strain.

The I-4627 yeast strain has thus been obtained in the following way:

selection of a yeast strain resistant to acetic acid, i.e. which has a delay of initiation of alcoholic fermentation of less than 14 h in the YFAc fermentation medium, selection of a yeast strain genetically modified by:

the insertion of at least one copy of an exogenous gene encoding a xylose isomerase (XI) of *Clostridium phytofermentans*, under the control of the pADH1 promoter and of the CYC1 terminator, the insertion of at least one copy of an exogenous gene encoding a xylitol dehydrogenase (XDH) of *Pichia stipitis*, under the control of the pADH1 promoter and of the CYC1 terminator.

at least one copy of the TAL1 endogenous gene placed under the control of the pPGK1 promoter, at least one copy of the TKL1 endogenous gene placed under the control of the pTDH3 promoter, at least one copy of the RPE1 endogenous gene placed under the control of the pTDH3 promoter.

at least one copy of the RKI1 endogenous gene placed under the control of the pTDH3 promoter, the insertion of at least one copy of an endogenous gene encoding a xylulokinase (XKS1) under the control of the pADH1 promoter and of the CYC1 terminator, and the deletion of at least one copy of the open reading frame of the GRE3 endogenous gene encoding an aldose reductase, crossing of said yeast strain resistant to acetic acid with said genetically modified yeast strain, so as to obtain a hybrid, directed evolution of said hybrid, so as to obtain the I-4627 yeast strain.

The I-4627 yeast strain comprises at least one copy of an exogenous gene encoding a xylose isomerase (XI) of *Clostridium phytofermentans*, under the control of the pADH1 promoter and of the CYC1 terminator, at least one copy of an exogenous gene encoding a xylitol dehydrogenase (XDH) of *Pichia stipitis*, under the control of the pADH1 promoter and of the CYC1 terminator, at least one copy of the TAL1 endogenous gene placed under the control of the pPGK1 promoter, at least one copy of the TKL1 endogenous gene placed under the control of the pTDH3 promoter, at least one copy of the RPE1 endogenous gene placed under the control of the pTDH3 promoter, at least one copy of the RKI1 endogenous gene placed under the control of the pTDH3 promoter, at least one copy of an endogenous gene encoding a xylulokinase (XKS1) under the control of the pADH1 promoter and of the CYC1 terminator, and at least one copy of the open reading frame of the GRE3 endogenous gene encoding an aldose reductase which has been deleted.

As for the 1-4538 yeast strain, the exogenous gene encoding a xylose isomerase (XI) of *Clostridium phytofermentans* is described in document DE102008031350 and the exogenous gene encoding a xylitol dehydrogenase (XDH) of *Pichia stipitis* is in Genbank.

The I-4627 yeast strain is devoid of any residual selectable marker.

The I-4627 yeast strain does not comprise a gene encoding an XR of exogenous origin, nor an araA, araB or AraD gene.

The I-4627 yeast strain is an industrial yeast strain and it is aneuploid.

The I-4627 yeast strain is prototrophic.

The resistance to acetic acid of the I-4627 yeast strain is less than that of the starting acetic acid-resistant yeast strain used for the crossing, but its resistance to acetic acid is widely acceptable for an industrial application.

Thus, the I-4627 yeast strain has a delay of initiation of alcoholic fermentation of less than 20 hours in the YFAc fermentation medium.

As regards the effectiveness on xylose, the I-4627 yeast strain converts approximately 60% of xylose to ethanol, under anaerobic conditions, in 60 hours, in the YFGX fermentation medium comprising 55 g of glucose and 45 g of xylose per kg of medium.

The I-4627 yeast strain is thus an original yeast strain which possesses resistance to acetic acid and which possesses the genetic machinery for metabolizing xylose, but which is not capable of metabolizing xylose for the purposes of the invention, i.e. which is incompatible with an industrial use with a view to ethanol production.

The inventors have therefore crossed the I-4538 yeast strain with the I-4627 strain, in order to obtain a yeast strain capable of metabolizing xylose and resistant to acetic acid.

An object of the present invention is therefore a method for obtaining a yeast strain capable of metabolizing xylose and resistant to acetic acid, comprising the steps of:

crossing the yeast strain deposited at the CNCM [National Collection of Microorganism Cultures] under number I-4538 with the yeast strain deposited at the CNCM under the number I-4627, so as to obtain at least one hybrid, selecting at least one hybrid capable of metabolizing xylose and resistant to acetic acid, so as to obtain a yeast strain capable of metabolizing xylose and resistant to acetic acid.

As defined above, the yeast strain capable of metabolizing xylose and resistant to acetic acid according to the invention has the following properties:

it converts at least 70%, preferably at least 80%, more preferentially at least 90% of xylose to ethanol in 60 hours in the YFGX fermentation medium comprising 55 g of glucose and 45 g of xylose per kg of fermentation medium, under anaerobic conditions, and it has a delay of initiation of alcoholic fermentation of less than 30 hours, preferably less than 29 hours, more preferentially less than 28 hours, in the YFAc fermentation medium comprising 4000 ppm of acetic acid at pH 4.4.

The crossing step is carried out according to the conventional techniques, such as those taught in chapter 7 "Sporulation and Hybridization of Yeast" by R. R. Fowell, of the reference book "The Yeasts", volume 1, edited by A. H. Rose and J. S. Harrison, 1969—Academic Press.

In order to improve the efficiency of the method for obtaining a yeast strain according to the invention, it is particularly advantageous to perform a selection on the segregants derived from the I-4538 yeast strain and/or on the segregants derived from the I-4627 yeast strain.

The segregants of the I-4538 yeast strain which are used for the crossing are preferably selected on the basis of their ability to metabolize xylose.

The segregants of the I-4627 yeast strain that are used for the crossing are selected on the basis of their resistance to acetic acid.

An object of the present invention is thus a method as defined above, characterized in that said crossing step comprises:

a step of sporulation of the yeast strain deposited at the CNCM [National Collection of Microorganism Cultures] under number I-4538, so as to obtain at least one segregant X, an optional step of evaluation of the conversion of xylose to ethanol by at least one segregant X, a step of sporulation of the yeast strain deposited at the CNCM under number I-4627, so as to obtain at least one segregant Y, an optional step of evaluation of the resistance to acetic acid of at least one segregant Y, a step of hybridization of at least one segregant X with at least one segregant Y, said segregant X being capable of converting xylose to ethanol and/or said segregant Y having resistance to acetic acid, so as to obtain at least one hybrid.

The steps of sporulation, of evaluation of the conversion of xylose to ethanol and of evaluation of the resistance to acetic acid can be carried out in any desired order, as long as the sporulation of a given yeast strain is performed before the evaluation of its segregants.

For example, an object of the present invention is a method as defined above, characterized in that said crossing step comprises:

a step of sporulation of the yeast strain deposited at the CNCM [National Collection of Microorganism Cultures] under number I-4538, so as to obtain at least one segregant X, an optional step of measurement of the percentage of xylose converted to ethanol by at least one segregant X, under anaerobic conditions, in 60 hours in a fermentation medium comprising 55 g of glucose and 45 g of xylose per kg of said medium, a step of sporulation of the yeast strain deposited at the CNCM under number I-4627, so as to obtain at least one segregant Y, an optional step of measurement of the delay of initiation of alcoholic fermentation of at least one segregant Y in a fermentation medium comprising 4000 ppm of acetic acid at pH 4.4, a step of hybridization of at least one segregant X with at least one segregant Y, the segregant X converting at least 60% of xylose to ethanol in 60 hours and/or the segregant Y having a delay of initiation of alcoholic fermentation of less than 30 hours, so as to obtain at least one hybrid.

The steps of sporulation, of measurement of the percentage of xylose converted to ethanol and of measurement of the delay of initiation of alcoholic fermentation can be carried out in any desired order, as long as the sporulation of a given yeast strain is performed before the measurement of the selection parameter applied to the segregants of this strain.

The inoculation used for measuring the percentage of xylose converted to ethanol by at least one segregant of the I-4538 yeast strain is preferably 0.25 g of dry matter/kg of fermentation medium.

The fermentation medium used for measuring the percentage of xylose converted to ethanol by at least one segregant of the I-4538 yeast strain is preferably the YFGX fermentation medium.

The segregants of the I-4538 yeast strain are naturally less effective than the starting aneuploid strain in terms of metabolizing xylose. Consequently, the selection criterion applied regarding the conversion of xylose to ethanol is less demanding than the ability of the starting I-4538 yeast strain.

Thus, in one advantageous embodiment, a segregant of the I-4538 yeast strain is selected if, under anaerobic conditions, it converts at least 60% of xylose to ethanol in 60 hours in a fermentation medium comprising 55 g of glucose and 45 g of xylose per kg of said medium, preferably at least 65% of xylose, even more preferentially at least 70% of xylose.

In order to optimize the duration of the segregant selection step, it is possible to measure the conversion of xylose to ethanol by the segregants of the I-4538 yeast strain over the course of a shorter period, for example over the course of 48 hours.

Thus, in another advantageous embodiment, a segregant of the I-4538 yeast strain is selected if, under anaerobic conditions, it converts at least 60% of xylose to ethanol in 48 hours in a fermentation medium comprising 55 g of glucose and 45 g of xylose per kg of said medium, preferably at least 65% of xylose, even more preferentially at least 70% of xylose.

In one advantageous embodiment, a segregant of the I-4627 yeast strain is selected if it has a delay of initiation of alcoholic fermentation of less than 30 hours, preferably less than 29 hours, more preferentially less than 28 hours, in a fermentation medium comprising 4000 ppm of acetic acid at pH 4.4.

However, surprisingly, the majority of the segregants of the I-4627 yeast strain are more resistant to acetic acid than the starting I-4627 yeast strain, i.e. their delay of initiation of alcoholic fermentation is less than that of the starting I-4627 yeast strain.

The selection criterion applied regarding the resistance to acetic acid is therefore preferably more demanding.

Thus, in one particularly advantageous embodiment, a segregant of the I-4627 yeast strain is selected if it has a delay of initiation of alcoholic fermentation of less than 25 hours, preferably less than 20 hours.

The fermentation medium used for measuring the delay of initiation of alcoholic fermentation of at least one segregant of the I-4627 yeast strain is preferably the YFAc fermentation medium.

The inoculation used for measuring the delay of initiation of alcoholic fermentation of at least one segregant of the I-4627 yeast strain is preferably 0.25 g of dry matter/kg of fermentation medium.

The segregants of the I-4627 yeast strain can also be selected on their ability to convert xylose to ethanol.

However, surprisingly, the best hybrids have been obtained using segregants of the I-4627 strain selected only on the basis of their resistance to acetic acid.

Preferably, the hybridization step is carried out with:
at least one segregant X which converts at least 60% of xylose to ethanol, preferably at least 65% of xylose, even more preferentially at least 70% of xylose in 60 hours, preferably in 48 hours, and
at least one segregant Y which has a delay of initiation of alcoholic fermentation of less than 30 hours, preferably less than 29 hours, more preferentially less than 28 hours, more preferentially less than 25 hours, even more preferentially less than 20 hours.

The hybrids thus obtained are then selected on the basis of the two criteria: their ability to metabolize xylose and their resistance to acetic acid.

An object of the present invention is more particularly a method as defined above, characterized in that said step of selecting at least one hybrid capable of metabolizing xylose and resistant to acetic acid comprises the steps of:
measuring the percentage of xylose converted to ethanol by at least one hybrid under anaerobic conditions in 60 hours in a fermentation medium comprising 55 g of glucose and 45 g of xylose per kg of fermentation medium,
measuring the delay of initiation of alcoholic fermentation of at least one hybrid in a fermentation medium comprising 4000 ppm of acetic acid at pH 4.4,
selecting at least one hybrid which converts at least 70%, preferably at least 80° %, more preferentially at least 90% of xylose to ethanol in 60 hours and of which the delay of initiation of alcoholic fermentation is less than 30 hours, preferably less than 29 hours, more preferentially less than 28 hours,
so as to obtain a yeast strain capable of metabolizing xylose and resistant to acetic acid.

The order of the steps of measuring the percentage of xylose converted to ethanol and of measuring the delay of initiation of alcoholic fermentation is of no importance; they can be carried out one after the other, in one direction or the other, or at the same time.

The conditions for measuring the percentage of conversion of xylose to ethanol and the delay of initiation of alcoholic fermentation are as defined above.

An object of the present invention is thus particularly a method for obtaining a yeast strain capable of metabolizing xylose and resistant to acetic acid, comprising the steps of:
crossing of the yeast strain deposited at the CNCM [National Collection of Microorganism Cultures] under number I-4538 with the yeast strain deposited at the CNCM under number I-4627, said crossing step comprising the steps of:

sporulation of the yeast strain deposited at the CNCM under number I-4538, so as to obtain at least one segregant X, measurement of the percentage of xylose converted to ethanol by at least one segregant X in 60 hours, preferably in 48 hours, in a fermentation medium comprising 55 g of glucose and 45 g of xylose per kg of said medium, selection of at least one segregant X which converts at least 60% of xylose to ethanol in 60 hours, preferably in 48 hours, sporulation of the yeast strain deposited at the CNCM under number I-4627, so as to obtain at least one segregant Y, measurement of the delay of initiation of alcoholic fermentation by at least one segregant Y in a fermentation medium comprising 4000 ppm of acetic acid at pH 4.4, selection of at least one segregant Y which has a delay of initiation of alcoholic fermentation of less than 30 hours, hybridization of at least one segregant which converts at least 60% of xylose to ethanol in 60 hours, preferably in 48 hours, with at least one segregant Y which has a delay of initiation of alcoholic fermentation of less than 30 hours, so as to obtain at least one hybrid, selection of at least one hybrid capable of metabolizing xylose and resistant to acetic acid, said selection step comprising the steps of:

measuring the percentage of xylose converted to ethanol by at least one hybrid, under anaerobic conditions, in 60 hours, in a fermentation medium comprising 55 g of glucose and 45 g of xylose per kg of fermentation medium, measuring the delay of initiation of alcoholic fermentation of said at least one hybrid in a fermentation medium comprising 4000 ppm of acetic acid at pH 4.4, selecting at least one hybrid which converts at least 70%, preferably at least 80%, more preferentially at least 90% of xylose to ethanol in 60 hours and of which the delay of initiation of alcoholic fermentation is less than 30 hours, preferably less than 29 hours, more preferentially less than 28 hours, so as to obtain a yeast strain capable of metabolizing xylose and resistant to acetic acid.

As indicated above, the order of the steps of the crossing step is of no importance, just as the order of the steps of the step of selecting at least one hybrid is of no importance.

Preferably, the hybridization step is carried out between:
at least one segregant X which converts at least 60% of xylose to ethanol, preferably at least 65% of xylose, even more preferentially at least 70% of xylose, in 60 hours, preferably in 48 hours, and at least one segregant Y which has a delay of initiation of alcoholic fermentation of less than 30 hours, preferably less than 29 hours, more preferentially less than 28 hours, even more preferentially less than 25 hours, even more preferentially less than 20 hours.

The method according to the invention can optionally comprise a directed evolution step.

In one advantageous embodiment of the invention, the directed evolution step is carried out on a hybrid not selected during the selection step of the method for obtaining a yeast strain capable of metabolizing xylose and resistant to acetic acid as defined above, with a view to rendering said hybrid capable of metabolizing xylose to ethanol and/or rendering it resistant to acetic acid.

An object of the present invention is thus also a method as defined above for obtaining a yeast strain capable of metabolizing xylose and resistant to acetic acid, comprising the steps of:

crossing of the yeast strain deposited at the CNCM [National Collection of Microorganism Cultures] under number I-4538 with the yeast strain deposited at the CNCM under number I-4627, so as to obtain at least one hybrid, directed evolution of at least one hybrid, selection of at least one hybrid capable of metabolizing xylose and resistant to acetic acid, so as to obtain a yeast strain capable of metabolizing xylose and resistant to acetic acid.

The directed evolution step comprises the following sub-steps:

mutagenesis. so as to obtain mutants, and multiplication of the mutants, in cyclic cultures, under hypoxic conditions, in a culture medium comprising xylose and/or a fermentation inhibitor.

To simplify, the mutants obtained at the end of the directed evolution step are still described as hybrids.

The expression "under hypoxic conditions" signifies under conditions of oxygen deficiency. An oxygen deficiency is defined herein by an oxygen percentage of less than 20% of the air. The mutagenesis step is preferably a "moderate" mutagenesis, i.e. obtained by exposure of the yeast cells to UV radiation at 254 nm of between 100 and 500 J/cm$^2$, for example 300 J/cm$^2$. These conditions cause a mortality rate of only 7% to 160% of the cell population subjected to the UV radiation.

The mortality rate is determined by plating out, on dishes of medium of which the carbon source is glucose, an identical volume of the cell suspension before and after mutagenesis and by comparing the number of colonies after 48 hours of growth.

The multiplication of the mutants in cyclic cultures, under hypoxic conditions, in a culture medium comprising xylose and/or an inhibitor comprises, for example:

a) the culture of the cell population subjected to the mutagenesis, in a culture medium, with stirring, under hypoxic conditions, preferably at 32° C., b) the sampling of a volume of the culture obtained in step a), for example one ml, and re-inoculating it into a culture medium having the same composition as in step a), steps a) and b) being repeated at least 3 times, preferably at least 4 times, for example 6 times, 7 times or 8 times.

When a fermentation inhibitor is present in the culture medium during the multiplication of the mutants, it is preferably acetic acid.

In one preferred embodiment of the invention, the multiplication of the mutants in cyclic cultures under hypoxic conditions is carried out in a culture medium comprising xylose and in the absence of acetic acid.

The culture medium for the multiplication of the mutants comprises, for example, 7% of xylose.

An example of a culture medium for the multiplication of the mutants is the YFX medium having the following composition: 70 g/kg of xylose, 5 g/kg of yeast extract, 4.7 g/kg of DAP (diammonium phosphate), 11.5 g/kg of citric acid, 13.5 g/kg of sodium citrate, 1 ml/kg of Tween 80, 2 ml/kg of ZnSO$_4$ (at 10.6 g/l), 2.5 ml/kg of MgSO$_4$.7H$_2$O (at 400 g/l), 1 ml/kg of thiamine (at 18.24 g/l), 1 ml/kg of pyridoxine (at 5.28 g/l), 1 ml/kg of biotin (at 1.76 g/l), 1 ml/kg of pantothenate (at 3.8 g/l), 2.5 ml/kg of nicotinic acid (at 8 g/l), 1 ml/kg of mesoinositol (at 50 g/l), 1 ml/kg of riboflavin (at 1 g/l), 1 ml/kg of para-aminobenzoate (at 1.2 g/l), pH adjusted to 4.4 with KOH.

The hypoxic conditions are, for example, obtained by virtue of a partial overpressure in the equipment used (for example, flasks or fermenters) due to an overpressure subsequent to the production of $CO_2$ produced during the fermentation, and to the absence of aeration.

Preferably, the duration of the culture a) is such that all of the xylose of the medium is consumed.

The duration of a culture is, for example, from 1 week to 48 hours.

The number of cultures carried out is variable, for example from 5 to 20.

In one preferred embodiment, the directed evolution step comprises a substep of selection of the non-respiratory-deficient mutants.

A non-respiratory-deficient mutant is a mutant capable of multiplying under conditions of oxidative metabolism.

In particular, a non-respiratory-deficient mutant is capable of multiplying, under aerobic conditions, at 30° C., in a medium which contains glycerol as sole carbon source, for example a medium comprising 20 g/kg of glycerol, 5 g/kg of ammonium sulfate and 1.7 g/kg of YNB (Yeast Nitrogen Base) medium, for example the YNB medium from Difco.

When the culture medium does not comprise a fermentation inhibitor, a substep of multiplication in a culture medium comprising acetic acid can be carried out after certain or each substep(s) of multiplication in cyclic cultures, in order to verify that the medium still contains at least one mutant resistant to acetic acid.

The duration of the multiplication in a culture medium comprising acetic acid is preferably greater than 20 h and less than 75 h.

For example, the duration of the substep of multiplication in a culture medium comprising acetic acid is included from 70 h to 75 h.

It is also possible to carry out a step of selection of the mutants which have an appropriate growth rate, by culture in a medium comprising glucose, for example a medium comprising 20 g/l of glucose, and selection of the mutants which have the appropriate growth rate.

A directed evolution step can also be carried out using the hybrid selected at the end of the selection step of the process for obtaining a yeast strain capable of metabolizing xylose and resistant to acetic acid as defined above, for example in order to further improve its ability to metabolize xylose and/or its resistance to acetic acid.

An object of the present invention is also a yeast strain capable of metabolizing xylose and resistant to acetic acid, which can be obtained by means of the method as defined above.

The H1 yeast strain was thus obtained by means of the method for obtaining a yeast strain as defined above (cf. example 1).

The H1 yeast strain converts at least 90% of xylose to ethanol under anaerobic conditions in 60 hours in the YFGX medium and has a delay of initiation of alcoholic fermentation of less than 22 h in the YFAc fermentation medium.

An object of the present invention is also particularly a yeast strain capable of metabolizing xylose and resistant to acetic acid, obtained by means of the method as defined above, which is chosen from the yeast strain deposited at the CNCM [National Collection of Microorganism Cultures] under number I-4624, the yeast strain deposited at the CNCM under number I-4625 and the yeast strain deposited at the CNCM under number I-4626.

The I-4624, I-4625 and I-4626 strains are *Saccharomyces cerevisiae* strains deposited under the treaty of Budapest on May 24, 2012, with the CNCM (National Collection of Microorganism Cultures), 25, rue du Docteur Roux, 75724 Paris cedex 15, France.

The yeast strain number I-4624 converts at least 90% of xylose to ethanol under anaerobic conditions in 60 hours in the YFGX medium and has a delay of initiation of alcoholic fermentation of less than 23 hours in the YFAc fermentation medium.

The yeast strain number I-4625 converts at least 90% of xylose to ethanol under anaerobic conditions in 60 hours in the YFGX medium and has a delay of initiation of alcoholic fermentation of less than 23 hours in the YFAc fermentation medium.

The yeast strain number I-4626 converts at least 90% of xylose to ethanol under anaerobic conditions in 60 hours in the YFGX medium and has a delay of initiation of alcoholic fermentation of less than 27 hours in the YFAc fermentation medium.

An object of the present invention is also a yeast strain derived from a yeast strain according to the invention which shares the same properties.

Thus, an object of the present invention is also a yeast strain derived from a yeast strain according to the invention, characterized in that said derived yeast strain is capable of metabolizing xylose and is resistant to acetic acid.

A derived yeast strain is as defined above in the definitions.

An object of the present invention is also a yeast obtained by culturing a yeast strain as defined above or by culturing a derived yeast strain as defined above.

The yeasts are obtained by culturing a yeast strain according to the invention or a derived yeast strain according to the invention, in particular as described in the reference book "Yeast Technology", $2^{nd}$ edition, 1991, G. Reed and T. W. Nagodawithana, published by Van Nostrand Reinhold, ISBN 0-442-31892-8.

The industrial-scale multiplication of yeasts generally comprises at least the first two steps of the set of the following steps:
- multiplication of a yeast strain in several stages, first under semi-anaerobic conditions and then under aerobic conditions,
- separation by centrifugation of the resulting yeast from its culture medium, so as to obtain a liquid cream yeast containing approximately between 12% and 25% of dry matter, or even a higher amount of dry matter if the cream yeast is mixed with osmolyte products,
- filtration of the resulting liquid cream yeast, generally on a rotary filter under vacuum, so as to obtain a dehydrated fresh yeast containing from 26% to 35% of dry matter,
- mixing of said dehydrated fresh yeast, so as to obtain a homogeneous mass,
- extrusion of the resulting yeast, so as to obtain:
  - a pressed yeast in the form of fresh yeast cakes or of crumbled fresh yeast, containing approximately 30% of dry matter, or
  - a yeast in the form of particles, generally granules, if the yeast is intended to be dried,
- optionally, drying in a sparing manner, in a stream of hot air, for example by fluidization, of the yeast particles obtained by extrusion, so as to obtain dry yeast.

The drying step is preferably a sparing rapid drying in the presence of an emulsifier.

Among the emulsifiers which can be used during the drying step, sorbitan monostearate, used for example at a concentration of approximately 1.0% (by weight relative to the weight of dry yeast), may be chosen.

The yeasts according to the invention can be used in any possible form.

For example, an object of the present invention is a yeast as defined above, characterized in that it is in the form of cream yeast, of pressed yeast, of dried yeast or of deep-frozen yeast.

The yeasts according to the invention have the same properties as the yeast strain from which they are obtained by culturing, namely:
- the yeasts according to the invention are capable of metabolizing xylose and
- the yeasts according to the invention are resistant to acetic acid.

The yeasts according to the invention are particularly advantageous for the production of industrial alcohol, for example intended for biofuels or for chemical industries.

An object of the present invention is also a method for producing at least one fermentation product, comprising a step of fermentation, under anaerobic conditions, by a yeast as defined above in a fermentation medium.

The fermentation product is in particular chosen from ethanol, a metabolite obtained from ethanol or a secondary metabolite.

A preferred fermentation product according to the invention is ethanol.

The ethanol production is obtained by means of alcoholic fermentation.

Those skilled in the art know how to determine the appropriate conditions for an alcoholic fermentation.

By way of example, reference may be made to the alcoholic fermentation conditions described in the reference book "Yeast Technology", $2^{nd}$ edition, 1991. G. Reed and T. W. Nagodawithana, published by Van Nostrand Reinhold. ISBN 0-442-31892-8.

The fermentation medium comprises the following elements: at least one fermentable carbon source, at least one nitrogen source, at least one sulfur source, at least one phosphorus source, at least one source of vitamins and/or at least one source of minerals.

The carbon source is, for example, provided in the form of a sugar which can be immediately assimilated by the yeast, a pentose such as xylose, glycerol, ethanol and/or a mixture thereof.

The carbon source is preferably provided by a sugar which can be immediately assimilated by the yeast, and by xylose.

A sugar which can be immediately assimilated by the yeast is, for example, a simple sugar of glucose, fructose or galactose type, a disaccharide of sucrose type and/or a mixture of these sugars.

The carbon source can be provided in the form of a glucose syrup, a fructose syrup, molasses, low-grade run-off 2 (low-grade run-off resulting from the 2nd crystallization of sugar), a hydrolyzate of all or part of a plant material, and/or a mixture thereof.

The nitrogen source is, for example, provided in the form of ammonium sulfate, ammonium hydroxide, diammonium phosphate, ammonia, urea and/or a combination thereof.

The sulfur source is, for example, provided in the form of ammonium sulfate, magnesium sulfate, sulfuric acid and/or a combination thereof.

The phosphorus source is, for example, provided in the form of phosphoric acid, potassium phosphate, diammonium phosphate, monoammonium phosphate, and/or a combination thereof.

The source of vitamins is, for example, provided in the form of molasses, yeast hydrolyzate, a solution of pure vitamin or of a mixture of pure vitamins, and/or a combination thereof.

The source of vitamins provides the yeast with all of the vitamins in amounts at least equivalent to those recommended in the reference handbooks. Several sources of vitamins can be combined.

The source of minerals is, for example, provided in the form of molasses, a mixture of mineral salts, and/or a combination thereof.

The source of minerals provides the yeast with all of the macroelements and trace elements in amounts at least equivalent to those recommended in the reference handbooks. Several sources of minerals can be combined.

The same substance can provide several different elements.

An object of the present invention is particularly a method as defined above, for producing at least one fermentation product, preferably ethanol, comprising a step of fermentation, under anaerobic conditions, by a yeast as defined above in a fermentation medium comprising xylose and/or at least one fermentation inhibitor.

The fermentation inhibitor is, for example, chosen from an organic acid, furfural, HMF (hydroxymethylfurfural), one or more phenolic compounds, and the osmotic pressure.

The organic acid is, for example, chosen from acetic acid, lactic acid, formic acid and levulinic acid.

In one preferred embodiment, said at least one fermentation inhibitor is acetic acid.

The osmotic pressure exists, for example, in a hydrolyzate of all or part of a plant material.

The osmotic pressure then originates in particular from the saline load provided during the method for obtaining said hydrolyzate.

The fermentation medium is as defined above.

The fermentation medium preferably comprises at least 0.2% of xylose, the percentage being expressed by weight/weight of the fermentation medium.

A preferred fermentation medium comprises 20% to 7% of xylose.

In one preferred embodiment of the invention, the fermentation medium also comprises a sugar which can be immediately assimilated by the yeast, for example glucose.

The fermentation medium comprises, for example, from 2% to 7% of xylose and from 0.5% to 15% of glucose.

In one preferred embodiment, the fermentation medium comprises xylose, glucose and acetic acid.

An object of the present invention is particularly a method as defined above, for producing at least one fermentation product, preferably ethanol, characterized in that said fermentation medium comprises at least one hydrolyzate of all or part of a plant material.

A hydrolyzate of all or part of a plant material can be obtained by means of a step of pretreatment of the plant material, for example at high temperature and in the presence of organic acids or solvents, optionally followed by a partial or total hydrolysis of the sugar polymers, enzymatically and/or chemically and/or thermally.

The hydrolyzate of all or part of a plant material therefore comprises a mixture of sugars originating from the hydrolysis of sugar polymers, such as cellulose, hemicellulose and starch.

A fermentation medium may also comprise a hydrolyzate of all or part of a plant material and sucrose.

An object of the present invention is also the use of a yeast as defined above, for producing at least one fermentation product, preferably in a fermentation medium comprising xylose and/or at least one fermentation inhibitor.

The fermentation product is as defined above.
The fermentation product is preferably ethanol.
The fermentation medium is as defined above.
The fermentation inhibitor is as defined above.

Other characteristics and advantages of the invention will emerge even more clearly on reading the following exemplary embodiments which illustrate the invention without limiting it, and for the understanding of which reference will be made to the appended drawings.

Example 1: Obtaining a Yeast Strain Capable of Metabolizing Xylose and Resistant to Acetic Acid Materials and Methods
(i) Fermentation Media The propagation medium used for the propagation of a yeast strain comprises 10 g/kg of yeast extract, 10 g/kg of peptone and 20 g/kg of glucose.

The YFGX culture medium described below is used for measuring the conversion of xylose to ethanol.

The YFAc culture medium described below is used for measuring the resistance to acetic acid.

The YFGX-Ac culture medium described below is used for evaluating the yeast strains in a culture medium which contains at the same time xylose, glucose and a fermentation inhibitor, acetic acid.

|  | YFGX | YFGX-Ac |
| --- | --- | --- |
| Glucose | 55 g/kg | 55 g/kg |
| Xylose | 45 g/kg | 45 g/kg |
| Yeast extract | 10 g/kg | 10 g/kg |
| Peptone | 10 g/kg | 10 g/kg |
| Acetic acid | 2000 ppm | 8000 ppm |
| Adjustment of pH with KOH | pH 5 | pH 5 |

In the YFGX medium, the acetic acid concentration of 2000 ppm at pH 5 has no inhibitory effect.

On the other hand, in the YFGX-Ac medium, the acetic acid concentration of 8000 ppm at pH 5 has an inhibitory effect.

|  | YFAc |
| --- | --- |
| Glucose | 150 g/kg |
| Yeast extract | 5 g/kg |
| DAP (Diammonium phosphate) | 4.7 g/kg |
| Citric acid | 11.5 g/kg |
| Acetic acid | 4 g/kg |
| Sodium citrate | 13.5 g/kg |
| Tween 80 | 1 ml/kg |
| ZnSO$_4$ (10.6 g/l) | 2 ml/kg |
| MgSO$_4$·7H$_2$O (400 g/l) | 2.5 ml/kg |
| Thiamine (18.24 g/l) Vit B1 | 1 ml/kg |
| Pyridoxine (5.28 g/l) Vit B6 | 1 ml/kg |
| Biotin (1.76 g/l) | 1 ml/kg |
| Pantothenate (3.8 g/l) | 1 ml/kg |
| Nicotinic acid (8 g/l) | 2.5 ml/kg |
| Mesoinositol (50 g/l) | 1 ml/kg |
| Riboflavin (1 g/l) | 1 ml/kg |
| Para-aminobenzoate (1.2 g/l) | 1 ml/kg |
| YFX | |
| Xylose | 70 g/kg |
| Yeast extract | 5 g/kg |
| DAP (Diammonium phosphate) | 4.7 g/kg |
| Citric acid | 11.5 g/kg |
| Sodium citrate | 13.5 g/kg |
| Tween 80 | 1 ml/kg |
| ZnSO$_4$ (10.6 g/l) | 2 ml/kg |
| MgSO$_4$·7H$_2$O (400 g/l) | 2.5 ml/kg |
| Thiamine (18.24 g/l) Vit B1 | 1 ml/kg |
| Pyridoxine (5.28 g/l) Vit B6 | 1 ml/kg |
| Biotin (1.76 g/l) | 1 ml/kg |
| Pantothenate (3.8 g/l) | 1 ml/kg |
| Nicotinic acid (8 g/l) | 2.5 ml/kg |
| Mesoinositol (50 g/l) | 1 ml/kg |
| Riboflavin (1 g/l) | 1 ml/kg |
| Para-aminobenzoate (1.2 g/l) | 1 ml/kg |

Adjustment of the pH to 4.4 with KOH (ii) Yeast Strain Propagation

The yeast strain propagation is carried out in two steps: a preculture step followed by a culture step.

The preculture is carried out by inoculating a loop of the yeast strain into 5 ml of the propagation medium as defined above.

After 24 h of culture at 30° C. in a medium aerated by stirring, 2 ml of this preculture are removed and inoculated into 50 ml of propagation medium.

This culture is carried out for 24 h at 30° C. in a medium aerated by stirring.

The conversion of xylose to ethanol and the resistance to acetic acid are measured on the cells of yeast resulting from this culture.

(iii) Measurement of the Conversion of Xylose to Ethanol

In order to determine the conversion of xylose to ethanol, 0.25 g of dry matter of the yeast strain propagated as indicated above are inoculated per kg of YFGX medium.

The fermentation is carried out at 32° C., under anaerobic conditions, with moderate stirring.

The ethanol and also xylose and glucose concentrations are measured by HPLC.

The following formula is then used to obtain the degree of conversion of xylose to ethanol:

$$\% \text{ conversion} = \frac{[\text{xylose}]_{initial} - [\text{xylose}]_{final}}{[\text{xylose}]_{initial}} \times 100$$

in which $[\text{xylose}]_{initial}$ corresponds to the xylose concentration in the medium at the time of the inoculation with the yeast strain and $[\text{xylose}]_{final}$ corresponds to the xylose concentration in the culture medium at 60 hours (starting from the inoculation).

(iv) Measurement of the Resistance to Acetic Acid

The resistance to acetic acid of a yeast strain is determined by the delay of initiation of alcoholic fermentation.

0.25 g of dry matter of the yeast strain propagated as indicated above are inoculated per kg of YFAc medium.

The fermentation is carried out under anaerobic conditions, at 32° C., with moderate stirring.

The ethanol production is measured indirectly by measuring the loss of mass of the fermentation flask, this loss of mass correlating directly with the alcohol production.

The alcoholic fermentation curve indicating the loss of mass as a function of time is produced.

The point of intersection between the x-axis and the maximum derivative of the loss of mass is determined: it corresponds to the delay of initiation of fermentation.

It should be noted that the maximum derivative of the loss of mass gives the same result as the maximum derivative of the alcohol production rate, if the alcoholic fermentation curve indicates the alcohol production as a function of time instead of the loss of mass as a function of time.

The more the duration obtained is restricted, the shorter the delay of initiation of fermentation and the more resistant the yeast strain is to acetic acid.

(v) Crossing

The starting strains used for the crossing are the I-4538 yeast strain and the I-4627 yeast strain.

Step 1: Yeast Strain Growth

A loop of the starting strain (conserved at −80° C.) is inoculated at the surface of the agar of a Petri dish of medium A.

The composition of medium A is the following: 10 g of yeast extract, 10 g of peptone, 20 g of glucose, 20 g of agar, pH 6.2+/−0.2, water qs 1 l.

The Petri dish is then incubated for 24 hours at 30° C.

Step 2: Sporulation on Medium 2

A loop of the previous culture is inoculated at the surface of the agar of a Petri dish of medium B.

The composition of medium B is the following: 6.5 g of sodium acetate, 15 g of agar, pH 6.5-7, water qs 1 l.

The Petri dish is incubated for 96 hours at 25° C. The biomass obtained at the surface of the dish is then harvested in 500 µl of sterile water, 25 µl of zymolyase are added to 100 µl of this suspension. The suspension is incubated for 30 minutes at 30° C., before being plated out onto an agar dish of medium 1. The tetrad dissection is preferably carried out 20 minutes later.

Step 3: Tetrad Dissection

The tetrads are dissected with a Singer micromanipulator, then the Petri dish is incubated for 48 hours at 30° C.

Step 4: Segregant Storage

The segregants are then stored at −80° C. in medium 1 comprising 20% of glycerol.

Step 5: Selection of the I-4538 Yeast Strain Segregants

The I-4538 yeast strain segregants are selected on their ability to convert xylose to ethanol.

The xylose conversion is measured as in (iii), using a segregant propagated as in (ii) for the yeast strain, except that the measurement is carried out at 48 hours instead of 60 hours.

The segregants selected convert at least 70% of the xylose at 48 hours.

The Mat a or Mat alpha sex type of the segregants selected is determined by PCR.

Step 6: Selection of the I-4627 Strain Segregants

The I-4627 yeast strain segregants are selected on the basis of their resistance to acetic acid. The resistance to acetic acid is evaluated as in (iv), using a segregant propagated as in (ii) for the yeast strain.

The segregants selected have a delay of initiation of fermentation of less than 25 hours.

The Mat a or Mat alpha sex type of the segregants selected is determined by PCR.

Step 7: Crossing and Selection of Hybrids

A loop of a Mat alpha haploid segregant is inoculated at the surface of the agar of a Petri dish of medium A. A loop of a Mat a haploid segregant is mixed with the deposit of the Mat alpha strain.

The composition of medium A is the following: 10 g of yeast extract, 10 g of peptone, 20 g of glucose, 20 g of agar, pH 6.2+/−0.2, water qs 1 l.

The Petri dish is then incubated for 24 hours at 30° C. A loop of the mixture is inoculated at the surface of the agar of a Petri dish of medium A. This step is repeated 5 times.

During the final inoculation, the cells are streaked so as to obtain isolated colonies. Yeast cells are removed from each isolated colony and cultured, their genomic DNA is extracted and a PCR is carried out on this genomic DNA in order to verify that the Mat a and Mat alpha alleles are indeed present in one and the same yeast cell.

The yeast cells which have the Mat a and Mat alpha alleles are called hybrids.

The hybrids are then selected on the basis of two criteria: their ability to metabolize xylose and their resistance to acetic acid, which are evaluated as indicated in (iii) and (iv).

The hybrids selected are the following:
- the hybrids which have a delay of initiation of alcohol fermentation of less than 30 hours,
- the hybrids which convert at least 60% of xylose at 60 hours.

(vi) Directed Evolution

Directed evolution is the combination of a step of UV mutagenesis followed by an enrichment on a fermentation medium in which xylose constitutes the only carbon source.

Step 1:

During the UV mutagenesis, 15 ml of a suspension of yeast cells at 5% (in g of dry matter for 100 g of the suspension) are placed in a 9 cm Petri dish. The Petri dish is then placed under a UV radiation of 300 J/cm$^2$ at 254 nm.

Step 2:

The irradiated yeast cells are then inoculated in an amount of 1 g of dry matter/kg of YFX medium. After 96 hours of multiplication under hypoxic conditions at 32° C., 100 µl of the culture medium are used to inoculate 50 ml of a glycerol medium containing 20 g/kg of glycerol, 5 g/kg of ammonium sulfate and 1.7 g/kg of YNB (Yeast Nitrogen Base) medium from Difco. This second culture is carried out under aerobic conditions and at 30° C. for 48 hours.

1 ml of this culture is then removed to inoculate 170 ml of YFX medium.

This cycle is repeated 8 times.

Results

Several hybrids are obtained by crossing the I-4538 strain with the I-4627 strain, among which the H1 and H2 hybrids.

The H2 hybrid, which is not capable of metabolizing xylose for the purposes of the invention but which exhibits resistance to acetic acid, is subjected to a directed evolution step: the ED1, ED2 and ED3 hybrids are then obtained, corresponding respectively to the I-4624, I-4626 and I-4625 yeast strains.

Table 1 indicates the percentage of xylose converted to ethanol at 60 hours in the YFGX medium and the delay of initiation of alcoholic fermentation in the YFAc medium (in hours) of various yeast strains:
- the Ac control which is a non-genetically-modified yeast strain resistant to acetic acid, which is not therefore capable of metabolizing xylose,
- the I-4538 starting yeast strain which is very effective for the production of alcohol, but is not resistant to acetic acid,
- the I-4627 starting yeast strain which is resistant to acetic acid, but is not capable of metabolizing xylose for the purposes of the invention.
- the H1 hybrid which is a yeast strain which is capable of metabolizing xylose and which is resistant to acetic acid, the H2 hybrid which is not capable of metabolizing xylose for the purposes of the invention, but exhibits resistance to acetic acid, the ED1, ED2 and ED3 hybrids which are capable of metabolizing xylose and are resistant to acetic acid.

TABLE 1

| Yeast strains | Percentage of xylose converted to ethanol at 60 hours in the YFGX medium | Delay of initiation of alcoholic fermentation in the YFAc medium (in hours) |
|---|---|---|
| Ac control | 0 | 12 |
| I-4538 | 95 | 40 |
| I-4627 | 60 | 18 |
| H1 | 95 | 20 |
| H2 | 60 | 25 |
| ED1 (I-4624) | 95 | 22 |
| ED2 (I-4626) | 95 | 26 |
| ED3 (I-4625) | 95 | 22 |

Moreover, the ethanol production of the yeast strains is evaluated in the YFGX-Ac fermentation medium comprising at the same time, glucose, xylose and acetic acid as fermentation inhibitor.

The H1, ED1, ED2 and ED3 yeast strains according to the invention have an alcohol production which is clearly improved compared with the I-4538 parent yeast strain in this YFGX-Ac medium (cf FIG. 1).

Example 2: Alcohol Production in an Actual Application Medium Using the Yeast Strains According to the Invention Materials and Methods The alcohol production of the ED1, ED2 and ED3 yeast strains is evaluated in an actual application medium.

The alcohol production of the I-4538 parent yeast strain is also evaluated by way of comparison.

The evaluation of the alcohol production of the yeast strains is carried out on two different application media:

medium A comprising:
  a hemicellulosic substrate which corresponds to the liquid phase obtained after solid/liquid separation of the biomass having undergone a pretreatment and thermochemical hydrolysis of a wheat straw and which comprises predominantly xylose (48 g/kg), other sugars in small amount, and also fermentation inhibitors resulting from the physicochemical pretreatment of the lignocellulosic biomass, and
  nutrients (sources of nitrogen and phosphorus), medium B corresponding to medium A above supplemented with glucose, in order to mimic a hydrolyzate of lignocellulosic biomass, the hemicellulosic fraction of which has been hydrolyzed and the cellulosic fraction of which would have been partially hydrolyzed.

The initial pH of media A and B is adjusted to pH 5.5.

The fermenter is inoculated with 1.5 g/kg of dry matter of the yeast strain to be evaluated.

The alcoholic fermentation is carried out at 35° C.

A fermentation is also carried out at 32° C. with medium A.

Results

Figure 2:
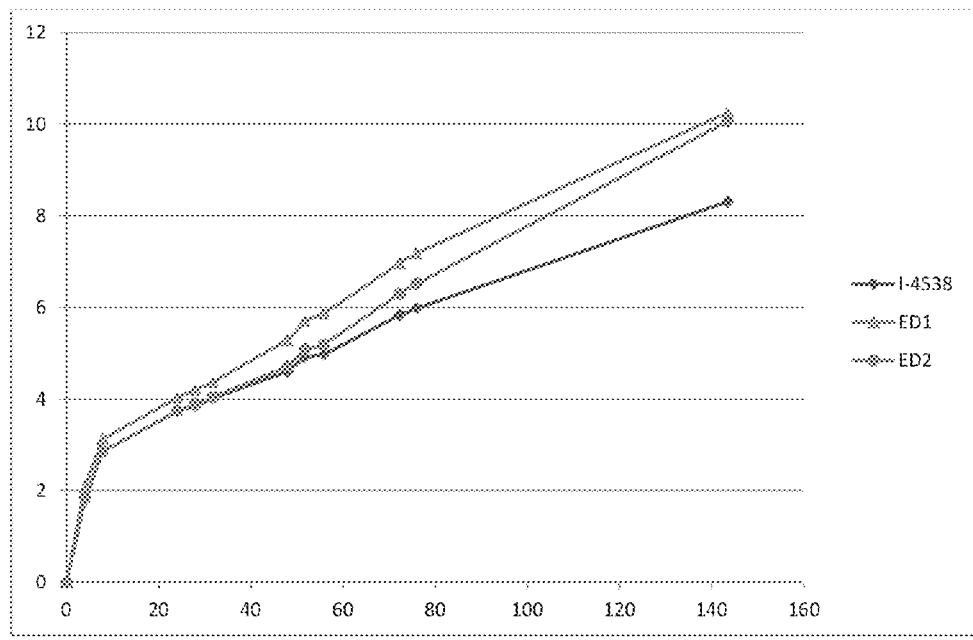
FIG. 2: Ethanol production (in g/kg of fermentation medium) over time (in hours) in medium A, at 32° C., by the I-4538 yeast strain (diamond), the ED1 yeast strain (triangle) and the ED2 yeast strain (circle).
Figure 3:
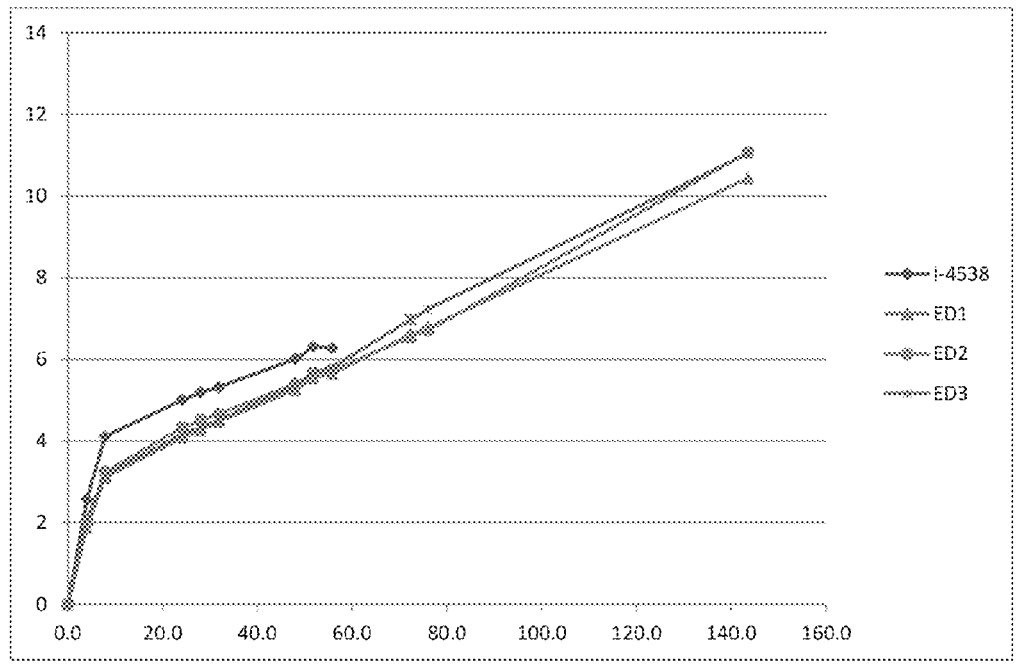
FIG. 3: Ethanol production (in g/kg of fermentation medium) over time (in hours) in medium A, at 35° C., by the I-4538 yeast strain (diamond), the ED1 yeast strain (triangle), the ED2 yeast strain (circle) and the ED3 yeast strain (cross).
Figure 4:
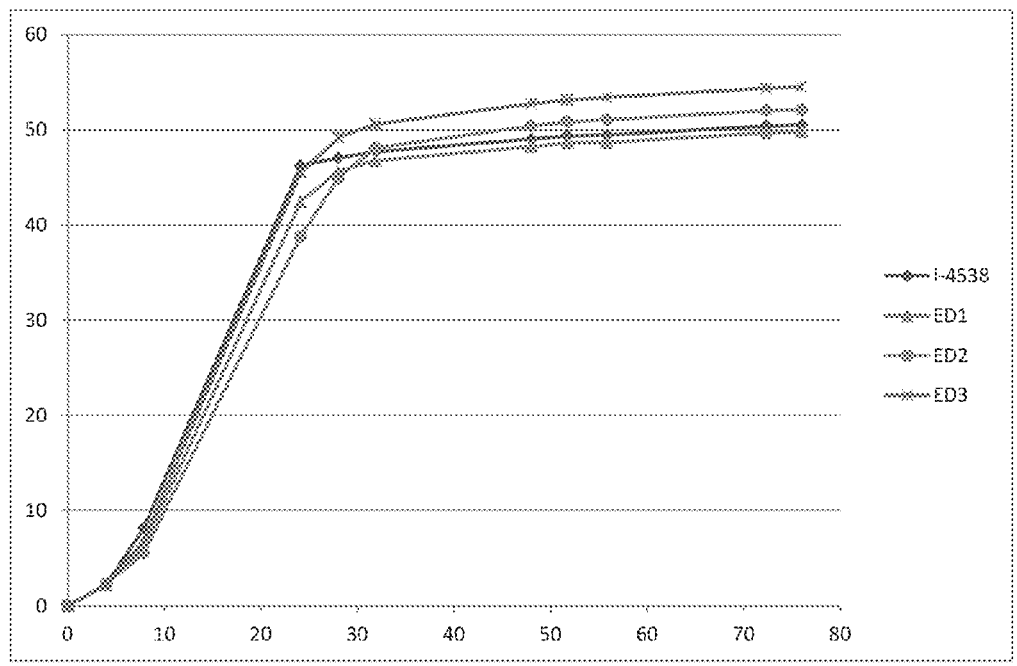
FIG. 4: Ethanol production (in g/kg of fermentation medium) over time (in hours) in medium B, at 35° C., by the I-4538 yeast strain (diamond), the ED1 yeast strain (triangle), the ED2 yeast strain (circle) and the ED3 yeast strain (cross).

The results obtained with medium A at 32° C. and 35° C. are given respectively in FIGS. 2 and 3, and the results with medium B at 35° C. in FIG. 4.

It should be noted that, in FIG. 3, the points have stopped at 60 h for the I-4538 yeast strain, since the plateau phase has already been reached.

The ED1 and ED2 hybrids show a real advantage in application medium A at 32° C. compared with the I-4538 parent yeast strain.

The ED1, ED2 and ED3 hybrids show a real advantage in application medium A at 35° C. compared with the 14538 parent yeast strain. Indeed, even though the ethanol production is better in the first 60 hours for the I-4538 yeast strain, the maximum amount of ethanol produced is 6.3 g per kg of medium, whereas amounts of ethanol greater than 10 g/kg are obtained with the ED1, ED2 and ED3 hybrids.

The ED1 and ED2 hybrids show, once again, a real advantage in application medium B at 35° C. compared with the I-4538 yeast strain. The ED3 hybrid is a little behind in this application medium.

The invention claimed is:

1. A method of obtaining a yeast strain of *Saccharomyces cerevisiae* capable of metabolizing xylose and resistant to acetic acid, comprising steps of:
   crossing the yeast strain of *Saccharomyces cerevisiae*, deposited on Oct. 5, 2011 at the CNCM under number I-4538 with the yeast strain of *Saccharomyces cerevisiae*, deposited on May 24, 2012 at the CNCM under number I-4627, so as to obtain at least one hybrid;
   measuring the percentage of xylose converted to ethanol by the at least one hybrid of *Saccharomyces cerevisiae* under anaerobic conditions in 60 hours in a fermentation medium comprising 55 g of glucose and 45 g of xylose per kg of said medium;
   measuring the delay of initiation of alcoholic fermentation of the at least one hybrid in a fermentation medium comprising 4000 ppm of acetic acid at pH 4,4; and
   identifying the at least one hybrid as a yeast strain of *Saccharomyces cerevisiae* capable of metabolizing xylose and resistant to acetic acid, if said at least one hybrid converts at least 70% of xylose to ethanol in 60 hours and exhibits a delay of initiation of alcoholic fermentation of less than 30 hours.

2. The method as claimed in claim 1, wherein said crossing step comprises steps of:
   a) sporulating the yeast strain of *Saccharomyces cerevisiae*, deposited on Oct. 5, 2011 at the CNCM under number I-4538, so as to obtain segregants, and selecting, among said segregants, at least one segregant X, if said at least one segregant X converts xylose to ethanol,
   b) sporulating the yeast strain of *Saccharomyces cerevisiae*, deposited on May 24, 2012 at the CNCM under number I-4627, so as to obtain segregants, and selecting, among said segregants, at least one segregant Y, if said at least one segregant Y is resistant to acetic acid, and
   c) hybridizing the at least one segregant X with the at least one segregant Y, so as to obtain the at least one hybrid.

3. The method as claimed in claim 2, wherein
   step a) further comprises: measuring, for each of the segregants obtained in step a), the percentage of xylose converted to ethanol under anaerobic conditions in 60 hours in a fermentation medium comprising 55 g of glucose and 45 g of xylose per kg of said medium, and the at least one segregant X is selected if said at least one segregant X converts at least 60% of xylose to ethanol in 60 hours;
   step b) further comprises: measuring, for each of the segregants obtained in step b), the delay of initiation of alcoholic fermentation in a fermentation medium comprising 4000 ppm of acetic acid at pH 4,4, and the at least one segregant Y is selected if said at least one segregant Y has a delay of initiation of alcoholic fermentation of less than 30 hours.

\* \* \* \* \*